(12) United States Patent
Hirao et al.

(10) Patent No.: US 12,046,365 B2
(45) Date of Patent: Jul. 23, 2024

(54) VEHICLE SEAT

(71) Applicant: TS TECH CO., LTD., Asaka (JP)

(72) Inventors: Yuya Hirao, Tochigi (JP); Katsuya Kawata, Tochigi (JP)

(73) Assignee: TS TECH CO., LTD., Asaka (JP)

( * ) Notice: Subject to any disclaimer, the term of this patent is extended or adjusted under 35 U.S.C. 154(b) by 149 days.

(21) Appl. No.: 17/765,023

(22) PCT Filed: Sep. 17, 2020

(86) PCT No.: PCT/JP2020/035173
§ 371 (c)(1),
(2) Date: Mar. 30, 2022

(87) PCT Pub. No.: WO2021/065526
PCT Pub. Date: Apr. 8, 2021

(65) Prior Publication Data
US 2022/0375598 A1    Nov. 24, 2022

(30) Foreign Application Priority Data

Sep. 30, 2019    (JP) ................................. 2019-179994
Sep. 30, 2019    (JP) ................................. 2019-180005

(51) Int. Cl.
*B60N 2/02*    (2006.01)
*B60N 2/66*    (2006.01)
(Continued)

(52) U.S. Cl.
CPC ........... *G16H 40/67* (2018.01); *B60N 2/0268* (2023.08); *B60N 2/667* (2015.04); *B60N 2/90* (2018.02)

(58) Field of Classification Search
CPC .... B60N 2/0268; B60N 2/667; B60N 2/6671; B60N 2/6673
See application file for complete search history.

(56) References Cited

U.S. PATENT DOCUMENTS 8,662,483 B2 *  3/2014  Yamaguchi .............. B60N 2/72
                                                                  267/144
11,135,943 B2 * 10/2021  Onuma .................. B60N 2/686
(Continued)

FOREIGN PATENT DOCUMENTS

CN    104718106 A  *  6/2015
CN    218943717 U  *  5/2023
(Continued)

OTHER PUBLICATIONS

PCT International Search Report (w/ English translation) for corresponding Application No. PCT/JP2020/035173, mailed Nov. 10, 2020, 6 pages.
(Continued)

*Primary Examiner* — Timothy J Brindley
(74) *Attorney, Agent, or Firm* — Dority & Manning, P.A.

(57) ABSTRACT

A radio wave transmitting/receiving device is placed in a vehicle in such a way that the device is near the back of the seated person, and no discomfort is caused to the back of the seated person. The vehicle seat includes a seat cushion and a seatback connected to a rear part of the seat cushion. The seatback comprises a seatback frame including a left and a right side frame portion extending vertically, and an upper frame portion extending laterally between upper ends of the side frame portions, a pressure receiving member consisting of a plate member configured to support a back of a seated person and provided with a radio wave transmissive property, and supported by the seatback frame via an elastic member, and a radio wave transmitting/receiving device supported on a back surface of the pressure receiving member to irradiate radio wave to a seated person and receive radio wave reflected by the seated person.

9 Claims, 15 Drawing Sheets

(51) Int. Cl.
*B60N 2/90* (2018.01)
*G16H 40/67* (2018.01)

(56) References Cited

U.S. PATENT DOCUMENTS

| | | | |
|---|---|---|---|
| 2003/0006636 A1* | 1/2003 | Ligon, Sr. | A47C 7/465 |
| | | | 297/284.4 |
| 2006/0261653 A1* | 11/2006 | McMillen | A47C 7/465 |
| | | | 297/284.4 |
| 2014/0070584 A1* | 3/2014 | McMillen | B60N 2/02 |
| | | | 297/284.4 |
| 2016/0221481 A1* | 8/2016 | Sugiyama | B60N 2/4228 |
| 2018/0092552 A1 | 4/2018 | Sato | |
| 2018/0272906 A1* | 9/2018 | Onuma | B60N 2/682 |
| 2019/0248260 A1* | 8/2019 | Yoshikawa | B60N 2/2222 |
| 2020/0292686 A1* | 9/2020 | Murata | G01S 13/42 |
| 2023/0091178 A1* | 3/2023 | Murata | G01S 13/68 |
| | | | 342/27 |
| 2023/0339367 A1* | 10/2023 | Kowata | A61B 5/05 |

FOREIGN PATENT DOCUMENTS

| | | | | |
|---|---|---|---|---|
| CN | 116585109 A | * | 8/2023 | |
| DE | 20221092 U1 | * | 1/2005 | B60N 2/66 |
| JP | 2001-114026 | | 4/2001 | |
| JP | 2013-067322 | | 4/2013 | |
| JP | 2015-145244 | | 8/2015 | |
| JP | 2018175831 A | | 11/2018 | |
| JP | 2019-068363 | | 4/2019 | |
| JP | 2019187953 A | * | 10/2019 | |
| JP | 2023024251 A | * | 2/2023 | |
| KR | 101770213 B1 | * | 8/2017 | |
| WO | WO-03095262 A2 | * | 11/2003 | B60N 2/66 |
| WO | WO-2007145299 A1 | * | 12/2007 | B60N 2/6671 |
| WO | WO-2014024586 A1 | * | 2/2014 | B60N 2/4228 |
| WO | WO-2015106338 A1 | * | 7/2015 | |

OTHER PUBLICATIONS

Chinese Office Action (w/ Machine translation) for corresponding Application No. 202080069755.0, dated Mar. 18, 2024, 9 pages.

* cited by examiner

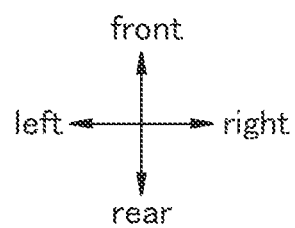
*Fig.5*
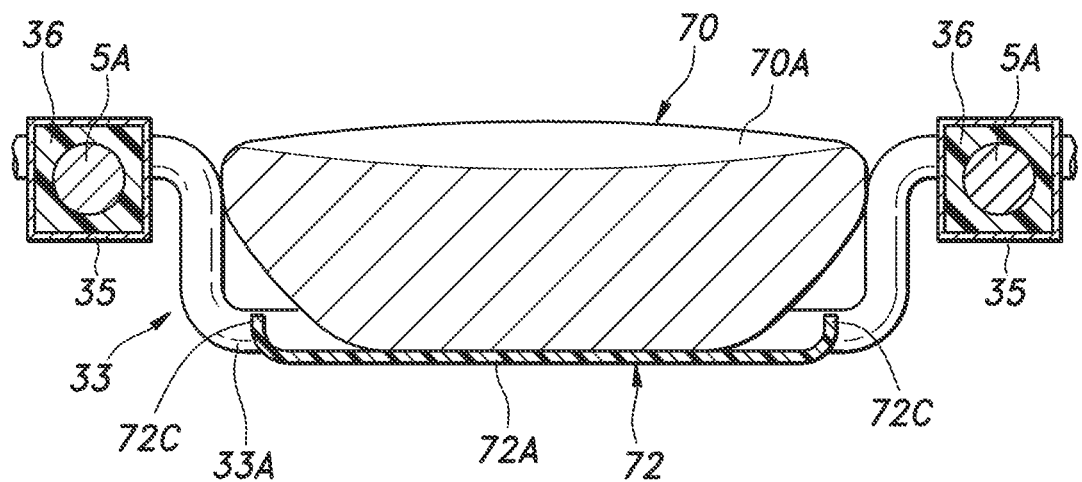

VEHICLE SEAT

CROSS REFERENCE TO RELATED APPLICATIONS

This application is the U.S. National Stage entry of International Application No. PCT/JP2020/035173 filed under the Patent Cooperation Treaty on Sep. 17, 2020, which claims priority to Japanese Patent Application No. 2019-179994 filed on Sep. 30, 2019 and Japanese Patent Application No. 2019-180005 filed on Sep. 30, 2019, all of which are incorporated herein by reference.

TECHNICAL FIELD

The present invention relates to a vehicle seat.

BACKGROUND OF THE INVENTION

A known vehicle seat is provided with a sensor on the seatback to detect the heartbeat of the seated person. For example, it is known to provide a helical antenna in the seatback to irradiate radio wave from the helical antenna to the back of the seated person, and detect a heartbeat signal from the reflected radio wave (See Patent Document 1, for instance).

PRIOR ART DOCUMENT(S)

Patent Document(s)

Patent Document 1: JP2016-174871A

In order to accurately detect the state of the seated person, the radio wave transmitting/receiving device such as an antenna needs to be positioned near the back of the seated person. On the other hand, in order to improve the comfort of the seated person, the radio wave transmitting/receiving device needs to be positioned so as not to cause discomfort to the back of the seated person.

SUMMARY OF THE INVENTION

Task to be Accomplished by the Invention

In view of such a problem of the prior art, a primary object of the present invention is to place a radio wave transmitting/receiving device in a vehicle in such a way that the device is near the back of the seated person, and no discomfort is caused to the back of the seated person.

Means to Accomplish the Task

To achieve such an object, a certain aspect of the present invention provides a vehicle seat (1) including a seat cushion (3) and a seatback (4) connected to a rear part of the seat cushion, wherein the seatback comprises, a seatback frame (21) including a left and a right side frame portion (26) extending vertically, and an upper frame portion (27) extending laterally between upper ends of the side frame portions, a pressure receiving member (22) consisting of a plate member configured to support a back of a seated person and provided with a radio wave transmissive property, and supported by the seatback frame via an elastic member (43, 44), and a radio wave transmitting/receiving device (70) supported on a back surface of the pressure receiving member to irradiate radio wave to a seated person and receive radio wave reflected by the seated person.

Thereby, the radio wave transmitting/receiving device can be positioned near the back of the seated person without causing any discomfort to the back of the seated person. Since the pressure receiving member is supported by the seatback frame via the elastic member, the pressure receiving member can be displaced under the pressure from the back of the seated person. Since the radio wave transmitting/receiving device is placed on the back of the pressure receiving member, the radio wave transmitting/receiving device can be displaced with the pressure receiving member so that no discomfort is caused to the back of the seated person.

In this configuration, preferably, one end of a control cable (55) for deforming the pressure receiving member is connected to the pressure receiving member, and the radio wave transmitting/receiving device is positioned so as not to overlap with the control cable in front view.

Thereby, the radio wave irradiated from the radio wave transmitting/receiving device and the radio wave reflected by the seated person are not blocked by the control cable.

In this configuration, preferably, the elastic member (43, 44) comprises a metal wire, and the radio wave transmitting/receiving device is positioned so as not to overlap with the elastic member in front view.

Thereby, the radio wave irradiated from the radio wave transmitting/receiving device to the seated person and the radio wave reflected by the seated person are not blocked by the elastic member.

In this configuration, preferably, the pressure receiving member is provided with a plurality of reinforcing ribs (48), and the radio wave transmitting/receiving device is positioned so as not to overlap with the reinforcing ribs in front view.

Thereby, the radio wave irradiated from the radio wave transmitting/receiving device to the seated person and the radio wave reflected by the seated person are not attenuated by the reinforcing ribs.

In this configuration, preferably, the pressure receiving member is provided with a plurality of openings (47), and the radio wave transmitting/receiving device is positioned so as not to overlap with the openings in front view.

Thereby, the paths of the radio wave irradiated from the radio wave transmitting/receiving device to the seated person and the radio wave reflected by the seated person are not affected by the openings.

In this configuration, preferably, the radio wave transmitting/receiving device is positioned on the pressure receiving member so as to be laterally offset from a center of the seatback in front view.

Thereby, the radio wave transmitting/receiving device can irradiate radio wave onto a surface part of a back of the seated person which is relatively actively displaced by pulsation.

In this configuration, preferably, the radio wave transmitting/receiving device is received in a pocket (81) provided on a back surface of the pressure receiving member.

Thereby, the connecting structure between the radio wave transmitting/receiving device and the pressure receiving member can be simplified.

In this configuration, preferably, one of the radio wave transmitting/receiving device and the pressure receiving member is provided with an engagement claw (83) for engaging another of the radio wave transmitting/receiving device and the pressure receiving member.

Thereby, the connecting structure between the radio wave transmitting/receiving device and the pressure receiving member can be simplified.

In this configuration, preferably, the pressure receiving member has a lateral width which changes along a vertical direction, and the radio wave transmitting/receiving device is provided at a vertical position having a largest lateral width in the pressure receiving member.

Thereby, the radio wave transmitting/receiving device can be positioned on the pressure receiving member in a stable manner.

In this configuration, preferably, the upper frame portion is provided with a left and a right support member (35) for supporting a left and a right pillar (5A) of a headrest (5), respectively, and the radio wave transmitting/receiving device is positioned laterally between the right and left support members in front view.

Thereby, the radio wave transmitting/receiving device can irradiate radio wave onto a surface part of a back of the seated person which is relatively actively displaced by pulsation.

Another aspect of the present invention provides a vehicle seat (1) including a seat cushion (3) and a seatback (4) connected to a rear part of the seat cushion, wherein the seatback comprises, a seatback frame (21) including a left and a right side frame portion (26) extending vertically, and an upper frame portion (27) extending laterally between upper ends of the side frame portions, and a radio wave transmitting/receiving device (70) supported by at least one of the side frame portions and the upper frame portion to irradiate radio wave to a seated person and receive radio wave reflected by the seated person.

Since the radio wave transmitting/receiving device is fixed to at least one of the side frame portions and the upper frame portion forming the structure of the seatback, the radio wave transmitting/receiving device can be fixed to an appropriate position on the seatback in a stable manner.

In this configuration, preferably, an upper end of the radio wave transmitting/receiving device is located below an upper end of the upper frame portion.

Thereby, the radio wave transmitting/receiving device can be positioned so as to correspond to the back of the seated person.

In this configuration, preferably, a bracket (72) is connected to the upper frame portion, and extends downward therefrom, and the radio wave transmitting/receiving device is attached to the bracket.

Thereby, the radio wave transmitting/receiving device can be positioned near the heart of the seated person.

In this configuration, preferably, the seatback frame further includes a cross member extending laterally between the side frame portions under the upper frame portion, and the bracket is connected to the cross member, the radio wave transmitting/receiving device being attached to the bracket.

Since the bracket is connected to the upper frame portion and the cross member, the position of the bracket is stabilized so that the position of the radio wave transmitting/receiving device can be stabilized.

In this configuration, preferably, the bracket extends vertically, and has an upper end part connected to the upper frame portion and a lower end part connected to the cross member.

Thereby, the position of the bracket is stabilized so that the position of the radio wave transmitting/receiving device can be stabilized.

In this configuration, preferably, the upper frame portion is provided with a left and a right support member (35) for supporting a left and a right pillar (5A) of a headrest (5), respectively, and the radio wave transmitting/receiving device is positioned laterally between the right and left support members in front view.

Thereby, the radio wave transmitting/receiving device can be positioned near the heart of the seated person.

In this configuration, preferably, each of the support members is formed in a tubular shape and extends vertically, and the upper end of the radio wave transmitting/receiving device is positioned below the upper ends of the support members and above the lower ends of the support members.

Thereby, the radio wave transmitting/receiving device can be positioned close to the heart of the seated person.

In this configuration, preferably, a front edge of the upper end of the radio wave transmitting/receiving device is positioned behind a front edge of the support members.

Thereby, the radio wave transmitting/receiving device is protected against a load from the front by the left and right support members. In addition, the radio wave transmitting/receiving device is less likely to affect the back of the occupant, and the occupant is less likely to experience discomfort due to the radio wave transmitting/receiving device on the back. Further, the radio wave transmitting/receiving device can be positioned in the dead space between the left and right support members.

In this configuration, preferably, the upper end of the radio wave transmitting/receiving device is positioned in front of the upper frame portion.

Thereby, the radio wave transmitting/receiving device can be positioned close to the heart of the seated person.

In this configuration, preferably, a front edge of the lower end of the radio wave transmitting/receiving device is positioned behind a front edge of the side frame portions at a same elevation.

Thereby, the radio wave transmitting/receiving device is less likely to affect the back of the occupant, and the occupant is less likely to experience discomfort due to the radio wave transmitting/receiving device on the back.

In this configuration, preferably, the seatback further includes a pad (23) supported by the seatback frame, and a back surface of the pad is formed with a recess (75) for receiving the radio wave transmitting/receiving device therein.

Thereby, the radio wave transmitting/receiving device is less likely to receive a load from the pad.

Effect of the Invention

According to a certain aspect of the present invention, the vehicle seat (1) includes a seat cushion (3) and a seatback (4) connected to a rear part of the seat cushion, wherein the seatback comprises, a seatback frame (21) including a left and a right side frame portion (26) extending vertically, and an upper frame portion (27) extending laterally between upper ends of the side frame portions, a pressure receiving member (22) consisting of a plate member configured to support a back of a seated person and provided with a radio wave transmissive property, and supported by the seatback frame via an elastic member (43, 44), and a radio wave transmitting/receiving device (70) supported on a back surface of the pressure receiving member to irradiate radio wave to the seated person and receive radio wave reflected by the seated person. Thereby, the radio wave transmitting/receiving device can be positioned near the back of the seated person without causing any discomfort to the back of the seated person. Since the pressure receiving member is supported by the seatback frame via the elastic member, the pressure receiving member can be displaced under the pressure from the back of the seated person. Since the radio wave transmitting/receiving device is placed on the back of the pressure receiving member, the radio wave transmitting/receiving device can be displaced with the pressure receiving member so that no discomfort is caused to the back of the seated person.

In this configuration, preferably, one end of a control cable (55) for deforming the pressure receiving member is connected to the pressure receiving member, and the radio wave transmitting/receiving device is positioned so as not to overlap with the control cable in front view. Thereby, the radio wave irradiated from the radio wave transmitting/receiving device and the radio wave reflected by the seated person are not blocked by the control cable.

In this configuration, preferably, the elastic member (43, 44) comprises a metal wire, and the radio wave transmitting/receiving device is positioned so as not to overlap with the elastic member in front view. Thereby, the radio wave irradiated from the radio wave transmitting/receiving device to the seated person and the radio wave reflected by the seated person are not blocked by the elastic member.

In this configuration, preferably, the pressure receiving member is provided with a plurality of reinforcing ribs (48), and the radio wave transmitting/receiving device is positioned so as not to overlap with the reinforcing ribs in front view. Thereby, the radio wave irradiated from the radio wave transmitting/receiving device to the seated person and the radio wave reflected by the seated person are not attenuated by the reinforcing ribs.

In this configuration, preferably, the pressure receiving member is provided with a plurality of openings (47), and the radio wave transmitting/receiving device is positioned so as not to overlap with the openings in front view. Thereby, the paths of the radio wave irradiated from the radio wave transmitting/receiving device to the seated person and the radio wave reflected by the seated person are not affected by the openings.

In this configuration, preferably, the radio wave transmitting/receiving device is positioned on the pressure receiving member so as to be laterally offset from a center of the seatback in front view. Thereby, the radio wave transmitting/receiving device can irradiate radio wave onto a surface part of a back of the seated person which is relatively actively displaced by pulsation.

In this configuration, preferably, the radio wave transmitting/receiving device is received in a pocket (81) provided on a back surface of the pressure receiving member. Thereby, the connecting structure between the radio wave transmitting/receiving device and the pressure receiving member can be simplified.

In this configuration, preferably, one of the radio wave transmitting/receiving device and the pressure receiving member is provided with an engagement claw (83) for engaging another of the radio wave transmitting/receiving device and the pressure receiving member. Thereby, the connecting structure between the radio wave transmitting/receiving device and the pressure receiving member can be simplified.

In this configuration, preferably, the pressure receiving member has a lateral width which changes along a vertical direction, and the radio wave transmitting/receiving device is provided at a vertical position having a largest lateral width in the pressure receiving member. Thereby, the radio wave transmitting/receiving device can be positioned on the pressure receiving member in a stable manner.

In this configuration, preferably, the upper frame portion is provided with a left and a right support member (35) for supporting a left and a right pillar (5A) of a headrest (5), respectively, and the radio wave transmitting/receiving device is positioned laterally between the right and left support members in front view. Thereby, the radio wave transmitting/receiving device can irradiate radio wave onto a surface part of a back of the seated person which is relatively actively displaced by pulsation.

According to another aspect of the present invention, the vehicle seat (1) includes a seat cushion (3) and a seatback (4) connected to a rear part of the seat cushion, wherein the seatback comprises, a seatback frame (21) including a left and a right side frame portion (26) extending vertically, and an upper frame portion (27) extending laterally between upper ends of the side frame portions, and a radio wave transmitting/receiving device (70) supported by at least one of the side frame portions and the upper frame portion to irradiate radio wave to a seated person and receive radio wave reflected by the seated person.

Since the radio wave transmitting/receiving device is fixed to at least one of the side frame portions and the upper frame portion forming the structure of the seatback, the radio wave transmitting/receiving device can be fixed to an appropriate position on the seatback in a stable manner.

In this configuration, preferably, an upper end of the radio wave transmitting/receiving device is located below an upper end of the upper frame portion.

Thereby, the radio wave transmitting/receiving device can be positioned so as to correspond to the back of the seated person.

In this configuration, preferably, a bracket (72) is connected to the upper frame portion, and extends downward therefrom, and the radio wave transmitting/receiving device is attached to the bracket.

Thereby, the radio wave transmitting/receiving device can be positioned near the heart of the seated person.

In this configuration, preferably, the seatback frame further includes a cross member extending laterally between the side frame portions under the upper frame portion, and the bracket is connected to the cross member, the radio wave transmitting/receiving device being attached to the bracket.

Since the bracket is connected to the upper frame portion and the cross member, the position of the bracket is stabilized so that the position of the radio wave transmitting/receiving device can be stabilized.

In this configuration, preferably, the bracket extends vertically, and has an upper end part connected to the upper frame portion and a lower end part connected to the cross member.

Thereby, the position of the bracket is stabilized so that the position of the radio wave transmitting/receiving device can be stabilized.

In this configuration, preferably, the upper frame portion is provided with a left and a right support member (35) for supporting a left and a right pillar (5A) of a headrest (5), respectively, and the radio wave transmitting/receiving device is positioned laterally between the right and left support members in front view.

Thereby, the radio wave transmitting/receiving device can be positioned near the heart of the seated person.

In this configuration, preferably, each of the support members is formed in a tubular shape and extends vertically, and the upper end of the radio wave transmitting/receiving device is positioned below the upper ends of the support members and above the lower ends of the support members.

Thereby, the radio wave transmitting/receiving device can be positioned close to the heart of the seated person.

In this configuration, preferably, a front edge of the upper end of the radio wave transmitting/receiving device is positioned behind a front edge of the support members.

Thereby, the radio wave transmitting/receiving device is protected against a load from the front by the left and right support members. In addition, the radio wave transmitting/receiving device is less likely to affect the back of the occupant, and the occupant is less likely to experience discomfort due to the radio wave transmitting/receiving device on the back. Further, the radio wave transmitting/receiving device can be positioned in the dead space between the left and right support members.

In this configuration, preferably, the upper end of the radio wave transmitting/receiving device is positioned in front of the upper frame portion.

Thereby, the radio wave transmitting/receiving device can be positioned close to the heart of the seated person.

In this configuration, preferably, a front edge of the lower end of the radio wave transmitting/receiving device is positioned behind a front edge of the side frame portions at a same elevation.

Thereby, the radio wave transmitting/receiving device is less likely to affect the back of the occupant, and the occupant is less likely to experience discomfort due to the radio wave transmitting/receiving device on the back.

In this configuration, preferably, the seatback further includes a pad (23) supported by the seatback frame, and a back surface of the pad is formed with a recess (75) for receiving the radio wave transmitting/receiving device therein.

Thereby, the radio wave transmitting/receiving device is less likely to receive a load from the pad.

BRIEF DESCRIPTION OF THE DRAWINGS

FIG. 5 is a horizontal sectional view showing a radio wave transmitting/receiving device, a bracket and a support member;

DETAILED DESCRIPTION OF THE PREFERRED EMBODIMENT(S)

A vehicle seat according to a first embodiment of the present invention as applied to an automobile seat is described in the following with reference to the appended drawings.

(Overall Structure)

Figure 1:
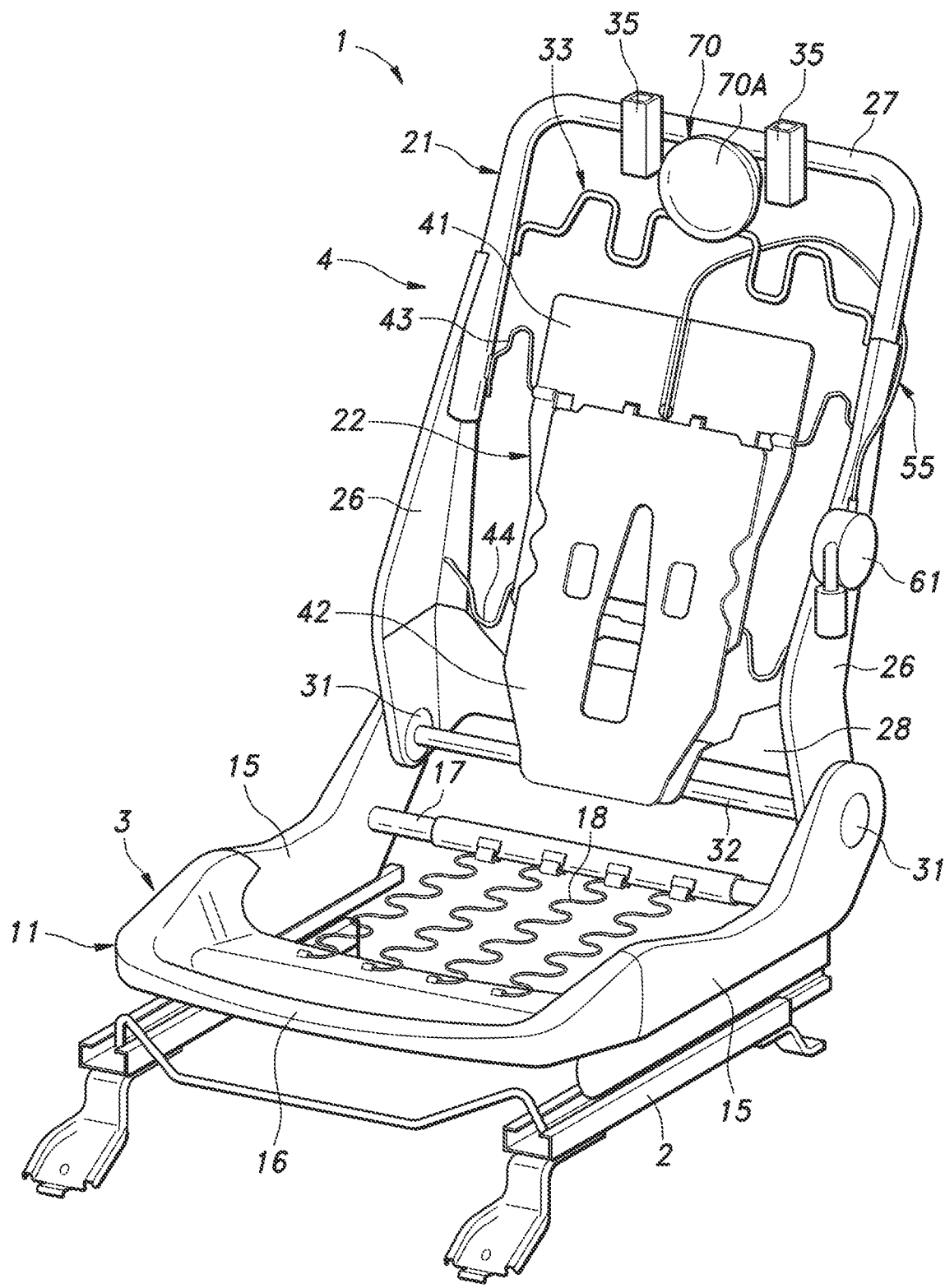
FIG. 1 is a perspective view of a frame of a seat according to a first embodiment of the present invention.
Figure 2:
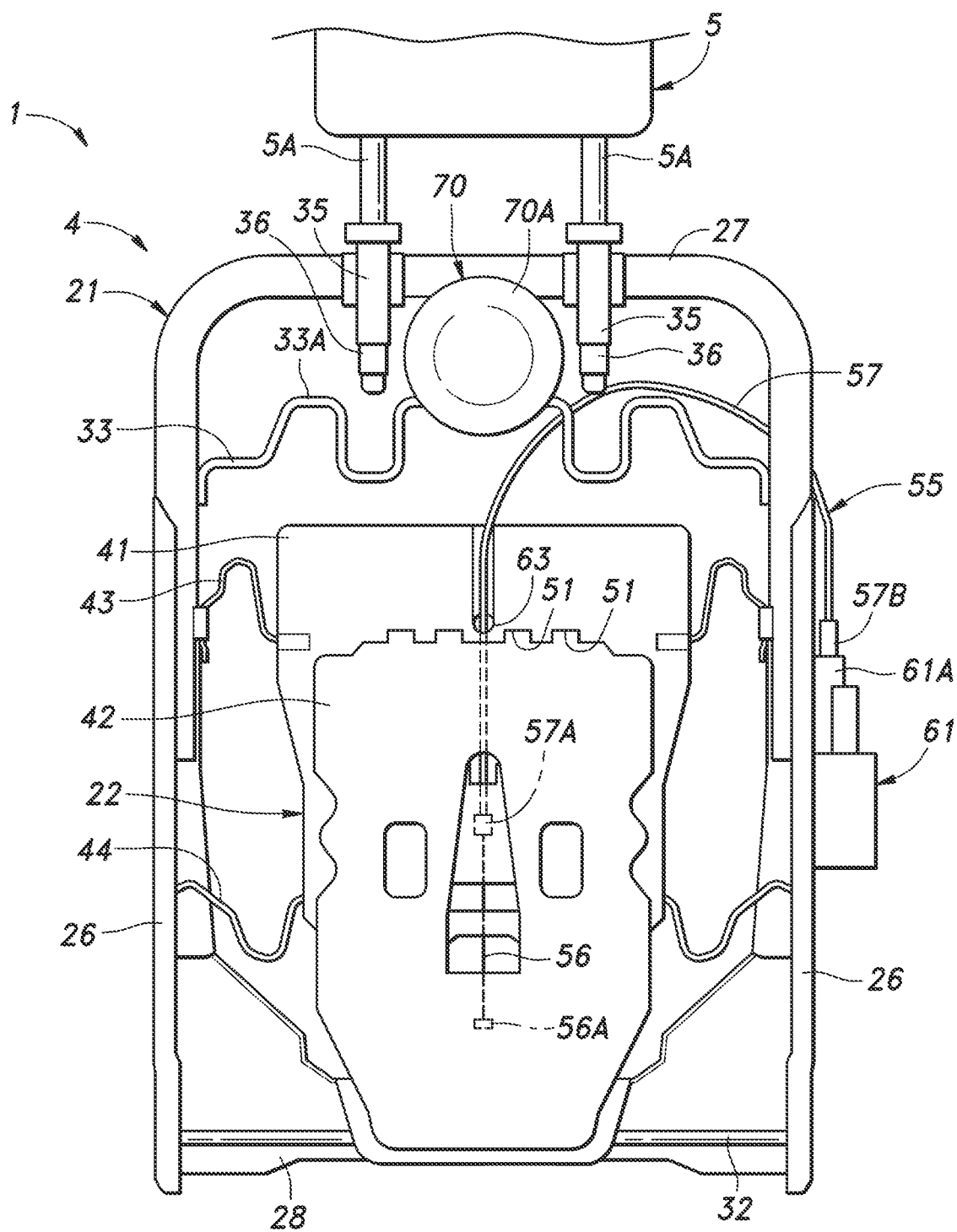
FIG. 2 is a front view of a seatback of the first embodiment with a pad and a skin member omitted from illustration.
Figure 3:
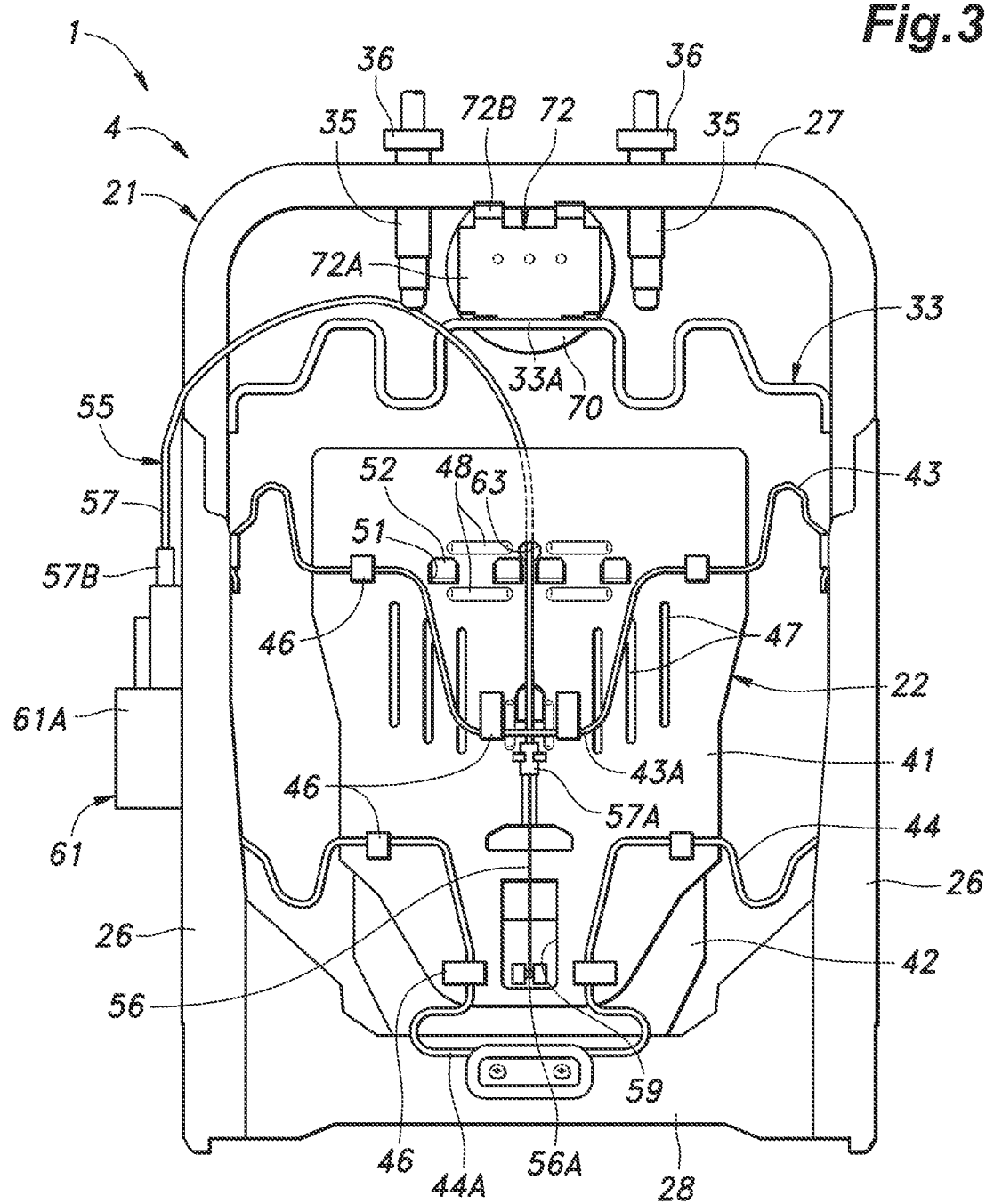
FIG. 3 is a rear view of the seatback of the first embodiment with a pad and a skin member omitted from illustration.

As shown in FIGS. 1 to 3, the seat 1 includes a seat cushion 3 provided on the floor of a passenger compartment via a slide rail device 2, a seatback 4 connected to a rear part of the seat cushion 3, and a headrest 5 provided on an upper part of the seatback 4.

The seat cushion 3 is provided with a seat cushion frame 11 forming a structural framework. A pad is supported on the seat cushion frame 11, and a skin member is placed on the outer surface of the pad. The seat cushion frame 11 includes a left and a right side frame portion 15 extending in the fore and aft direction, a front frame portion 16 extending laterally between the front ends of the left and right side frame portions 15, and a rear frame portion 17 extending laterally between the rear ends of the left and right side frame portions 15. The rear ends of the left and right side frame portions 15 extend rearward with an upward slant. A plurality of S-shaped springs 18 extending in the fore and aft direction are suspended between the front frame portion 16 and the rear frame portion 17.

The seatback 4 includes a seatback frame 21 forming a structural framework, a pressure receiving member 22 (lumbar support) supported by the seatback frame 21, and a pad 23 (see FIG. 6) supported by the seatback frame 21 and the pressure receiving member 22, and a skin member 24 (see FIG. 6) covering the outer surface of the pad 23. The seatback frame 21 includes a left and a right side frame portion 26 extending vertically, an upper frame portion 27 extending laterally between the upper ends of the left and right side frame portions 26, and a lower frame portion 28 extending laterally between the lower ends of the left and right side frame portions 26.

In the present embodiment, most of the left and right side frame portions 26 except the upper end parts thereof are formed of sheet metal members having major surfaces facing laterally. The upper frame portion 27 and the upper end parts of the left and right side frame portions 26 are formed by bending a pipe member having a circular cross section. The central part of the pipe member with respect to the lengthwise direction thereof extends laterally to form the upper frame portion 27, and the left and right end parts with respect to the lengthwise direction thereof are bent downward to form the upper end parts of the left and right side frame portions 26. The two ends of the pipe member extend along the inner surface of the sheet metal members forming the left and right side frame portions 26, and are welded to the corresponding sheet metal members. The lower frame portion 28 is formed of a sheet metal member and has a major surface that faces in the fore and aft direction. The left and right ends of the lower frame portion 28 are welded to the rear edges of the lower end parts of the corresponding side frame portions 26.

The lower ends of the left and right side frame portions 26 are connected to the rear ends of the corresponding side frame portions 15 via reclining mechanisms 31, respectively. The left and right side frame portions 26 are supported by the left and right side frame portions 15 via the reclining mechanisms 31 in an angularly adjustable manner. The left and right reclining mechanisms 31 are connected to each other by a connecting shaft 32.

The seatback frame 21 is further provided with a cross member 33 extending laterally between the left and right side frame portions 15 under the upper frame portion 27. The left and right ends of the cross member 33 are connected to the left and right side frame portions 26, respectively. In the present embodiment, the cross member 33 is formed by bending a metal rod (metal wire) having a circular cross section. The cross member 33 has a plurality of bent portions 33A that are bent so as to project upward. The upper end of each bent portion 33A extends linearly along the lateral direction.

The upper frame portion 27 is provided with a left and a right support member 35 for supporting the left and right pillars 5A of the headrest 5, respectively. The left and right support members 35 are each formed in a tubular shape with two open ends, and are connected to the upper frame portion 27 so that the axial direction thereof extends vertically. The left and right support members 35 are arranged symmetric to each other with respect to the laterally central line of the seatback 4. A space is defined between the left and right support members 35. A resin guide member 36 is inserted inside each support member 35. The guide member 36 is formed in a tubular shape, and the corresponding pillar 5A is inserted into the guide member 36.

The pressure receiving member 22 is a plate member that supports the back of the seated person, and is supported by the seatback frame 21 via elastic members 43 and 44. The pressure receiving member 22 includes a base plate 41 and a movable plate 42 supported by the base plate 41. The base plate 41 and the movable plate 42 are preferably formed of a resin material and have a flexibility. The elastic members 43 and 44 include a first elastic member 43 and a second elastic member 44 each consisting of a wirework spring. The first elastic member 43 and the second elastic member 44 are made of metal wire having elasticity. Each of the first elastic member 43 and the second elastic member 44 extends laterally, and is connected to the left and right side frame portions 15 at the left and right ends thereof, respectively. The base plate 41 is supported by the laterally central parts of the first elastic member 43 and the second elastic member 44.

The base plate 41 is supported by the first elastic member 43 and the second elastic member 44 so that the major surface thereof faces the fore and aft direction. A plurality of hook portions 46 for securing the first elastic member 43 and the second elastic member 44 are formed on the back surface of the base plate 41. The base plate 41 is positioned in front of the first elastic member 43 and the second elastic member 44 with the hook portions 46 engaging the first elastic member 43 and the second elastic member 44.

As shown in FIG. 3, a plurality of openings 47 are formed at appropriate positions of the base plate 41 and the movable plate 42 for the purpose of increasing the flexibility of the base plate 41 and the movable plate 42. Further, a plurality of reinforcing ribs 48 are formed at appropriate positions of the base plate 41 and the movable plate 42 for the purpose of locally increasing the rigidity of the base plate 41 and the movable plate 42.

Each of the first elastic member 43 and the second elastic member 44 is provided with a plurality of bent portions 43A and 44A. The first elastic member 43 extends along the back surface of an upper part of the base plate 41. The first elastic member 43 is provided with a first bent portion 43A protruding downward at a laterally central part thereof. The second elastic member 44 is positioned below the first elastic member 43. The second elastic member 44 extends along the back surface of a lower part of the base plate 41. The second elastic member 44 is provided with a second bent portion 44A protruding downward at a laterally central part thereof. The second bent portion 44A extends beyond the lower edge of the base plate 41, and is connected to the lower frame portion 28.

As shown in FIG. 2, the movable plate 42 is provided along the front surface of the base plate 41 and is connected to the base plate 41 at the upper edge thereof. The movable plate 42 is movable with respect to the base plate 41 except for the upper edge thereof. A plurality of locking holes 51 are passed through the base plate 41, and a plurality of engagement claws 52 are formed on the upper edge of the movable plate 42. The upper edge of the movable plate 42 is connected to the base plate 41 by hooking the engagement claws 52 into the corresponding locking holes 51. The lower edge of the movable plate 42 extends beyond the lower edge of the base plate 41. The lower edge of the movable plate 42 may extend beyond the upper edge of the lower frame portion 28 in front of the lower frame portion 28.

A control cable 55 is provided in order to displace the movable plate 42 with respect to the base plate 41 or to deform the movable plate 42. The control cable 55 includes an inner cable 56 and an outer tube 57 that slidably receives the inner cable 56. The first end 57A of the outer tube 57 is connected to a central part of the back surface of the base plate 41 in such a manner that the open end thereof faces downward. The first end 56A of the inner cable 56 extends downward out of the first end 57A of the outer tube 57, passes through a first insertion hole 59 formed in the base plate 41, and is connected to a lower part of the back surface of the movable plate 42. The second end 57B of the outer tube 57 is fixed to a casing 61A of a cable drive device 61. The second end (not shown in the drawings) of the inner cable 56 extends out of the second end 57B of the outer tube 57, and is connected to an output end (not shown in the drawings) of the cable drive device 61. The cable drive device 61 displaces the output end thereof by using the driving force of an electric motor, and pulls the second end of the inner cable 56 outward with respect to the second end 57B of the outer tube 57. The cable drive device 61 may be provided on either the outer side surface or the inner side surface of one of the side frame portions 15.

In the present embodiment, the control cable 55 extends upward from the first end 57A of the outer tube 57, passes through a second insertion hole 63 formed in the base plate 41, and extends to the front side of the base plate 41. The control cable 55 extends upward from the second insertion hole 63 along the front surface of the base plate 41 and extends beyond the upper edge of the base plate 41. The control cable 55 then curves laterally from the upper edge of the base plate 41 and extends to the cable drive device 61.

When the cable drive device 61 is operated, the inner cable 56 is pulled toward the cable drive device 61, and the first end 56A of the inner cable 56 moves toward the first end 57A of the outer tube 57, or upward. As a result, the inner cable 56 pulls the lower part of the movable plate 42 upward with respect to the base plate 41. At this time, since the upper edge of the movable plate 42 is connected to the base plate 41, the movable plate 42 is deformed such that the central part of the movable plate 42 projects forward with respect to the base plate 41. When the movable plate 42 projects forward with respect to the base plate 41, the shape of the front surface of the seatback 4 changes. As a result, the pressure applied to the back (lumbar region) of the seated person by the seatback 4 changes. The amount of deformation of the movable plate 42 can be adjusted by changing the driving amount of the cable drive device 61, or the pulled amount of the inner cable 56. When the cable drive device 61 releases the pulling force on the inner cable 56, the movable plate 42 returns to the initial shape thereof owing to the restoring force of the material of the movable plate 42.

As shown in FIG. 1, the seatback 4 is provided with a radio wave transmitting/receiving device 70 for acquiring biometric information of the seated person seated on the seat 1. The biometric information includes pulse (heartbeat) and blood pressure. The radio wave transmitting/receiving device 70 irradiates the seated person with radio wave, and receives the radio wave reflected by the seated person. The radio wave may be millimeter wave or microwave. The radio wave transmitting/receiving device 70 is connected to an electronic control device (not shown in the drawings) including a demodulation circuit and a signal processing circuit. The electronic control device may be provided on the back surface of the seatback 4 or the lower surface of the seat cushion 3, or may be provided on a part of the vehicle body remote from the seat 1. Further, the electronic control device may be integrated into a control device that controls other devices of the vehicle.

The radio wave transmitting/receiving device 70 and the electronic control device form a Doppler radar. The radio wave transmitting/receiving device 70 transmits radio wave toward the body surface of the back of the seated person, and receives the reflected radio wave reflected by the body surface of the back of the seated person. The electronic control device determines the relative velocity of the body surface of the back of the seated person with respect to the radio wave transmitting/receiving device 70 from the difference between the frequency of the transmitted radio wave and the frequency of the received radio wave (reflected radio wave) caused by the Doppler effect. Then, the electronic control device determines the pulse rate of the seated person according to the relation between the changes in the speed of the body surface of the back of the seated person relative to the radio wave transmitting/receiving device 70 over a prescribed time period and the pulse rate of the seated person.

The radio wave transmitting/receiving device 70 is provided with a casing 70A made of a material that transmits the transmitted radio wave and reflected radio wave. When the radio wave that is transmitted and reflected is millimeter wave, the casing 70A is preferably formed of polycarbonate, syndiotactic polystyrene, polypropylene, acrylonitrile-butadiene-styrene (ABS) resin or the like. The outer shape of the casing 70A may be bowl-shaped, rectangular, or the like.

As shown in FIGS. 3 to 6, a bracket 72 is connected to the upper frame portion 27. The bracket 72 is formed of a sheet metal member and has a flat plate-shaped main body 72A whose major surface faces in the fore and aft direction. The main body 72A is formed in a substantially rectangular shape, and a pair of opposite sides extend to the left and right. The bracket 72 is welded to the upper frame portion 27 at the upper end part of the main body 72A. At least one connecting piece 72B to be welded to the upper frame portion 27 may be provided at the upper end of the main body 72A. The main body 72A of the bracket 72 extends downward from the upper frame portion 27.

The bracket 72 is welded to the cross member 33 at the lower end of the main body 72A. As a result, the position of the bracket 72 can be stabilized, and the position of the radio wave transmitting/receiving device 70 can be stabilized. The bracket 72 may be welded to the upper end of the bent portion 33A located at the center of the cross member 33.

Figure 4:
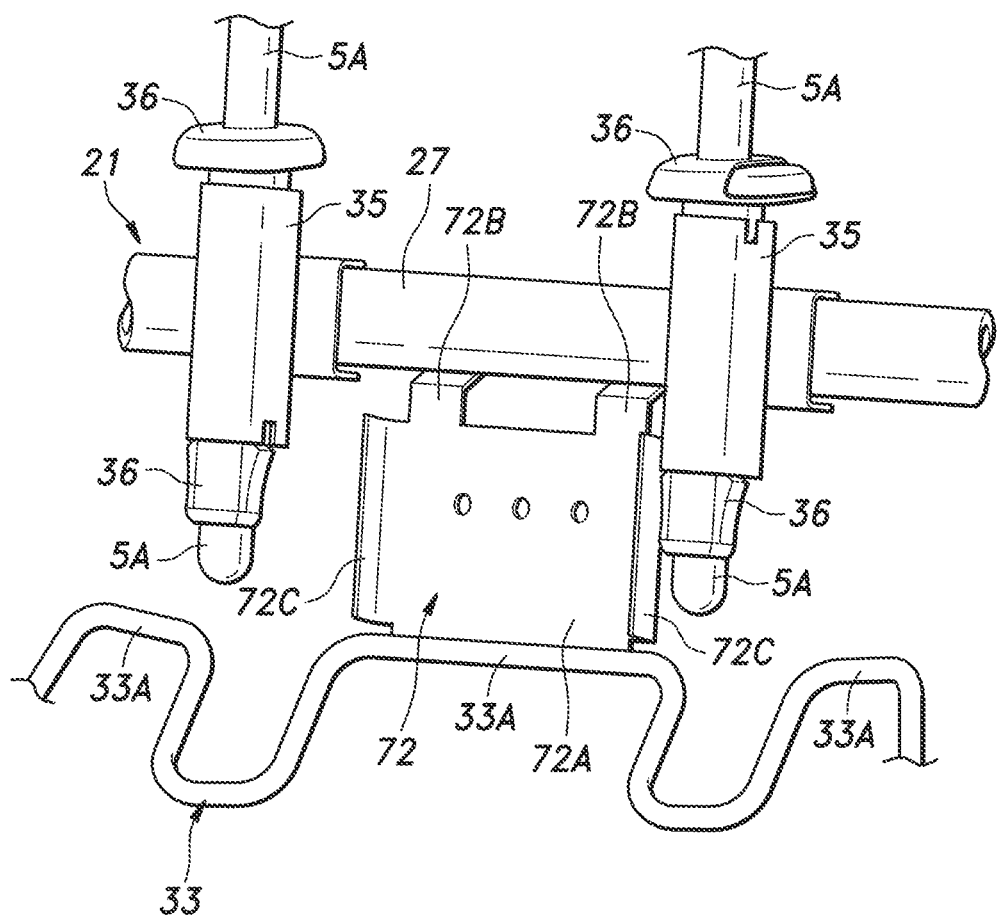
FIG. 4 is a perspective view of an upper structure of the seatback of the first embodiment as seen from the front.

As shown in FIGS. 3 and 4, the bracket 72 may be positioned between the left and right support members 35 in front view. The upper end part of the bracket 72 may be welded to a part of the upper frame portion 27 located between the left and right support members 35.

As shown in FIGS. 4 and 5, a pair of edge walls 72C are formed at the left and right side edges of the main body 72A of the bracket 72 by bending a part of the main body 72A at right angle. The edge walls 72C increases the rigidity of the bracket 72. Further, by providing the edge walls 72C, the occupant seated behind the seat 1 is prevented from coming into contact with the side edges of the bracket 72 even when the occupant hits the back surface of the seatback 4 as a result of the collision of the vehicle.

A radio wave transmitting/receiving device 70 is attached to the front surface of the main body 72A of the bracket 72. The radio wave transmitting/receiving device 70 may be fastened to the main body 72A with, for example, screws or the like. In the present embodiment, the casing 70A of the radio wave transmitting/receiving device 70 is formed in a bowl shape, and is positioned so that the radio wave transmitting direction faces forward. The orientation of the radio wave transmitting/receiving device 70 may be appropriately changed according to the desired measurement position. The radio wave emitted from the radio wave transmitting/receiving device 70 passes through the casing 70A, the pad 23, the skin member 24, and the clothes of the seated person. The radio wave transmitting/receiving device 70 detects the reflected radio wave reflected by the body surface of the back of the seated person as the received radio wave.

Figure 6:
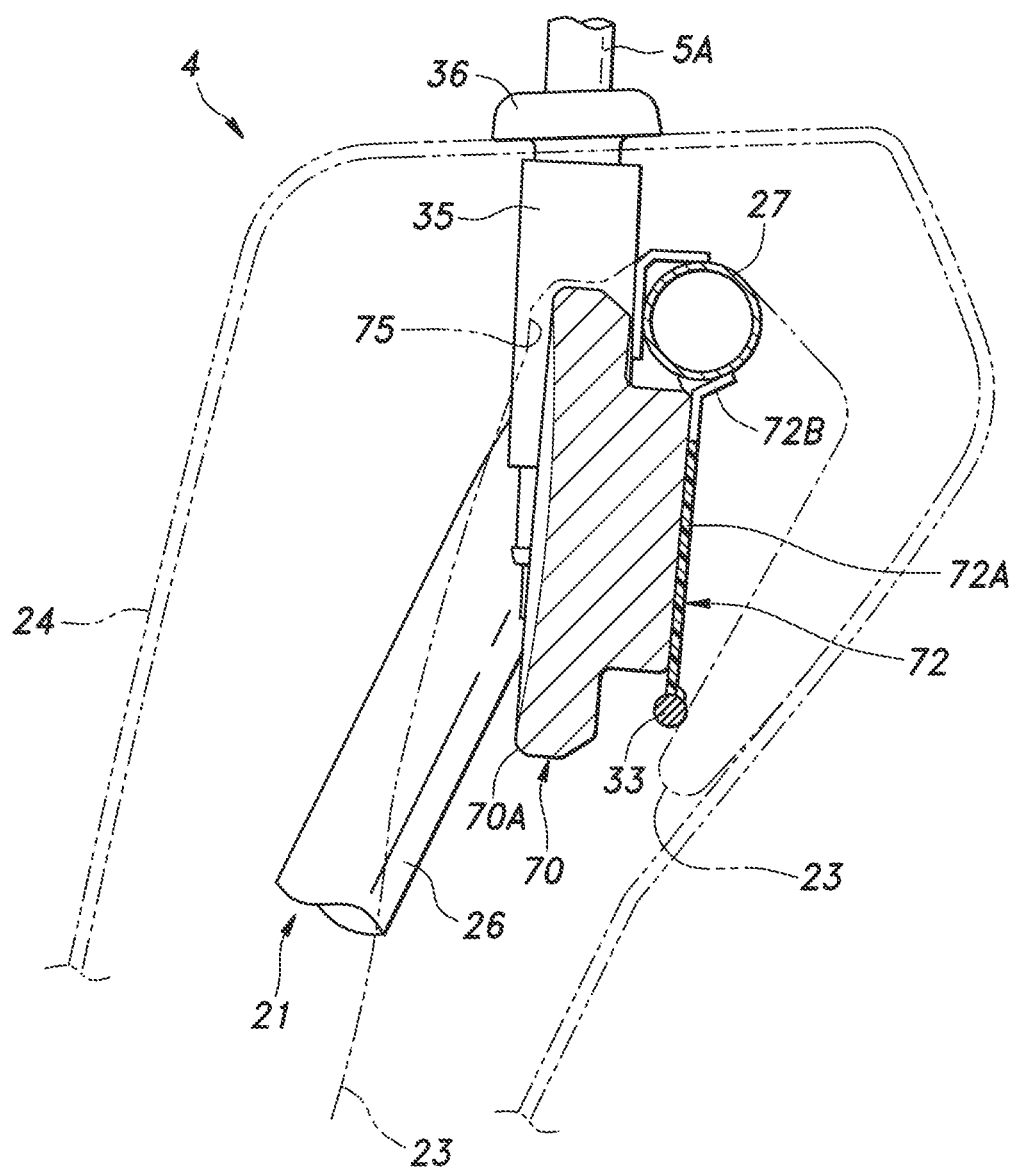
FIG. 6 is a vertical sectional view of the seatback of the first embodiment.

As shown in FIGS. 3 and 6, the upper end of the radio wave transmitting/receiving device 70 is preferably located below the upper end of the upper frame portion 27. As a result, the radio wave transmitting/receiving device 70 can be positioned so as to correspond to the back of the seated person. Further, preferably, the upper end of the radio wave transmitting/receiving device 70 is positioned below the upper end of the support members 35 and above the lower end of the support members 35. As a result, the radio wave transmitting/receiving device 70 can be positioned close to the heart of the seated person.

As shown in FIG. 6, in side view, the front edge of the upper end of the radio wave transmitting/receiving device 70 is preferably positioned behind the front edge of the support members 35. As a result, the radio wave transmitting/receiving device 70 is protected by the left and right support members 35 against the load from the front. In addition, the radio wave transmitting/receiving device 70 is less likely to affect the back of the occupant, and the occupant is less likely to experience discomfort due to the presence of the radio wave transmitting/receiving device 70 near the back of the occupant. Further, the radio wave transmitting/receiving device 70 can be accommodated in the dead space defined between the left and right support members 35.

Further, in side view, the front edge of the lower end of the radio wave transmitting/receiving device 70 may be positioned behind the front edge of the side frame portions 15 at the same elevation. As a result, the radio wave transmitting/receiving device 70 is less likely to cause discomfort to the occupant due to the presence of the radio wave transmitting/receiving device 70 near the back of the occupant.

Further, the upper end of the radio wave transmitting/receiving device 70 may be positioned in front of the upper frame portion 27. As a result, the radio wave transmitting/receiving device 70 can be positioned close to the heart of the seated person.

A recess 75 for receiving the radio wave transmitting/receiving device 70 is formed on the back surface of an upper part of the pad 23. When installing the pad 23 to the seatback frame 21, it is preferable that the radio wave transmitting/receiving device 70 is received by the recess 75 so as not to receive a load from the pad 23. Thus, the recess 75 is provided in order to avoid interference between the pad 23 and the radio wave transmitting/receiving device 70.

In the following will be described a second embodiment of the present invention in which the radio wave transmitting/receiving device 70 is supported by the pressure receiving member 22. As shown in FIGS. 7 to 11, in the second embodiment, the radio wave transmitting/receiving device 70 is supported on the back surface of the pressure receiving member 22. The pressure receiving member 22 according to the second embodiment is formed of a material having a favorable radio wave transmissibility for millimeter waves or microwaves. When the radio wave transmitted or received by the radio wave transmitting/receiving device 70 is a millimeter wave, the base plate 41 and the movable plate 42 forming the pressure receiving member 22 may be made of, for example, polycarbonate, syndiotactic polystyrene, polypropylene, acrylonitrile-butadiene-styrene (ABS) resin, or the like. In the second embodiment, the casing 70A of the radio wave transmitting/receiving device 70 is formed in the shape of a rectangular parallelepiped.

Figure 7:
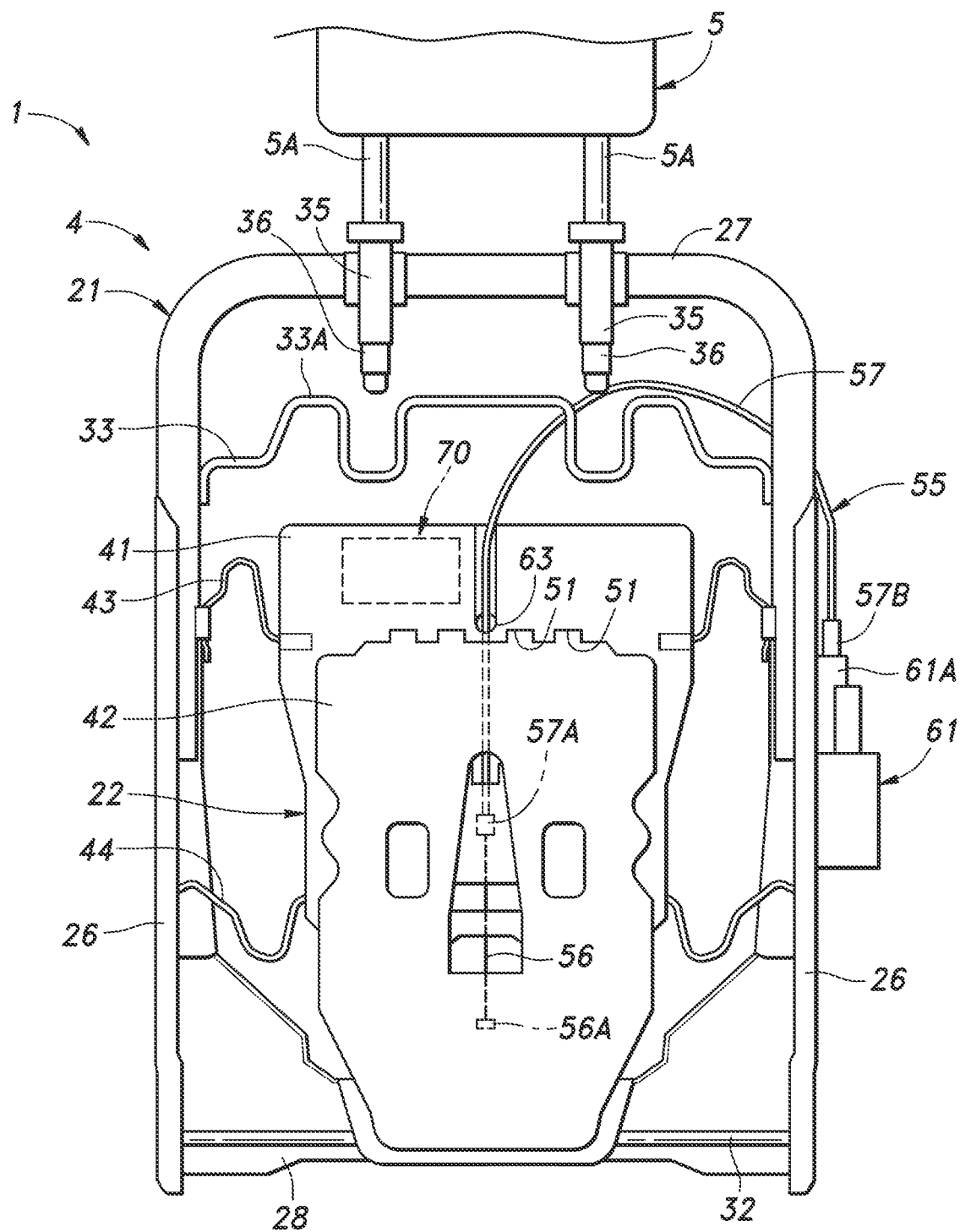
FIG. 7 is a front view of a seatback of according to a second embodiment of the present invention with a pad and a skin member omitted from illustration.
Figure 8:
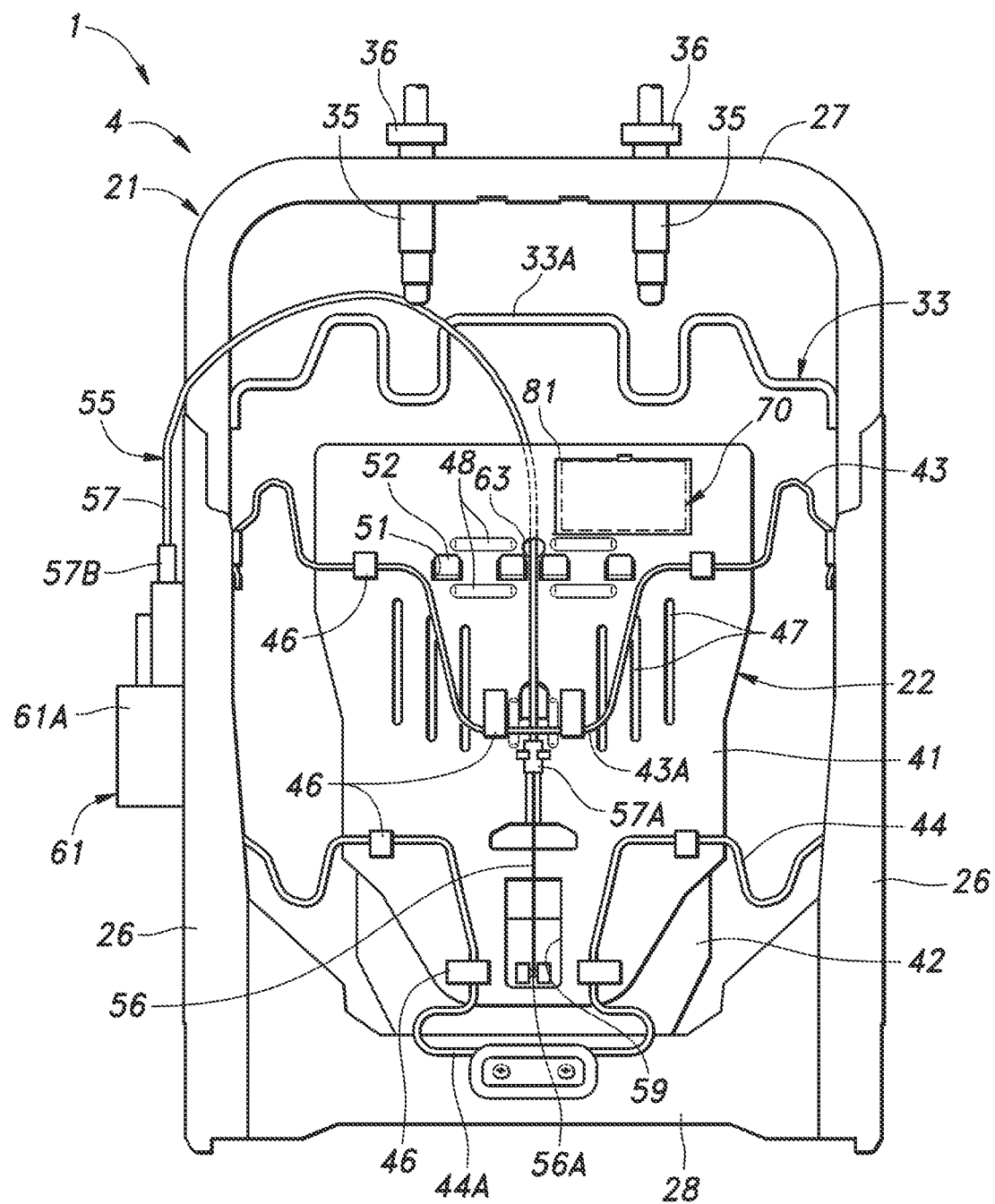
FIG. 8 is a rear view of the seatback of the second embodiment with a pad and a skin member omitted from illustration.

As shown in FIGS. 7 to 11, the radio wave transmitting/receiving device 70 is attached to the back surface of an upper part of the base plate 41 so that the radio wave may be transmitted through the base plate 41, and radiated in the forward direction. As shown in FIGS. 7 and 8, the radio wave transmitting/receiving device 70 is preferably positioned so as not to overlap with the movable plate 42 in front view. In the present embodiment, the lower edge of the radio wave transmitting/receiving device 70 is positioned above the upper edge of the movable plate 42. Further, the upper edge of the radio wave transmitting/receiving device 70 is positioned below the upper edge of the base plate 41.

The radio wave transmitting/receiving device 70 is positioned so as not to overlap with the control cable 55 in front view. Further, the radio wave transmitting/receiving device 70 is positioned so as not to overlap with the first elastic member 43 and the second elastic member 44 in front view. As a result, the radio wave transmitted from the radio wave transmitting/receiving device 70 and the radio wave reflected by the seated person are prevented from being blocked by the control cable 55, the first elastic member 43, or the second elastic member 44.

Further, the radio wave transmitting/receiving device 70 is positioned so as not to overlap with the reinforcing ribs 48 in front view. As a result, the radio wave transmitted from the radio wave transmitting/receiving device 70 and the radio wave reflected by the seated person are prevented from being attenuated by the reinforcing ribs 48.

The radio wave transmitting/receiving device 70 is preferably positioned on the base plate 41 of the pressure receiving member 22 so as to be displaced from the center of the seatback 4 to the left or right in front view. Further, the radio wave transmitting/receiving device 70 is preferably positioned on the base plate 41 so as to be laterally offset from the center of the base plate 41 in front view. As a result, the radio wave transmitting/receiving device 70 can irradiate a part of the back of the seated person whose body surface is comparatively actively moved by pulsation. The surface parts of the back of a human laterally offset from the center where the spine is located are known to move comparatively actively.

In the present embodiment, the radio wave transmitting/receiving device 70 is positioned laterally offset from the center so as not to overlap with the control cable 55 which is positioned along a laterally central part of the base plate 41 in front view.

Figure 9:
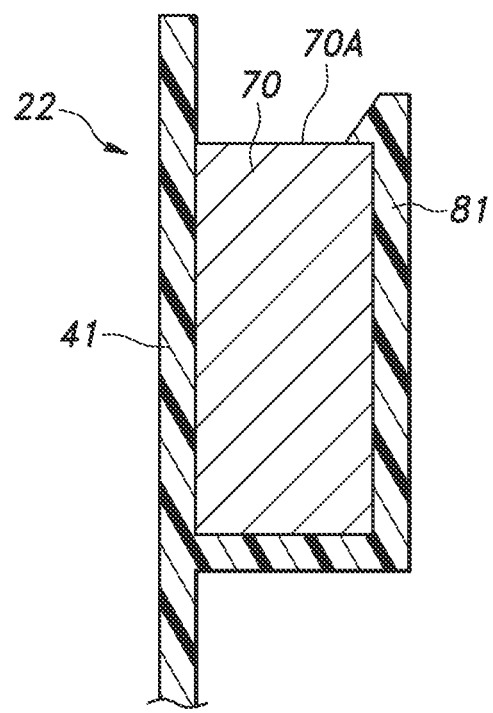
FIG. 9 is an example of a mounting structure for mounting a radio wave transmitting/receiving device to a base plate according to the second embodiment of the present invention.
Figure 10:
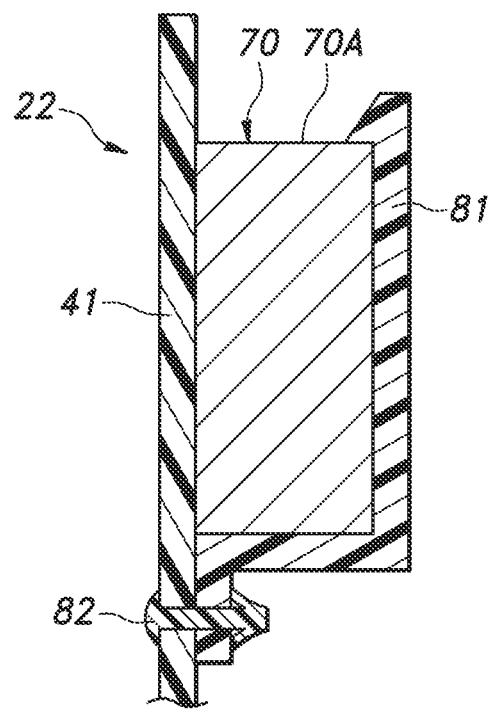
FIG. 10 is another example of a mounting structure for mounting a radio wave transmitting/receiving device to a base plate according to the second embodiment of the present invention.

An example of a structure for attaching the radio wave transmitting/receiving device 70 to the base plate 41 will be described in the following. For example, as shown in FIG. 9, the back surface of the base plate 41 may be provided with a pocket 81 that projects rearward and opens upward. The pocket 81 may be integrally molded with the base plate 41. Further, as shown in FIG. 10, the pocket 81 may also be formed as a separate member from the base plate 41, and attached to the base plate 41 by using a fastening member 82 such as a clip, a screw or an adhesive. Further, the pocket 81 may be connected to the base plate 41 by using an engagement claw or the like. The radio wave transmitting/receiving device 70 is supported by the base plate 41 by being fitted into the pocket 81. As a result, the connecting structure between the radio wave transmitting/receiving device 70 and the pressure receiving member 22 can be simplified.

Figure 11:
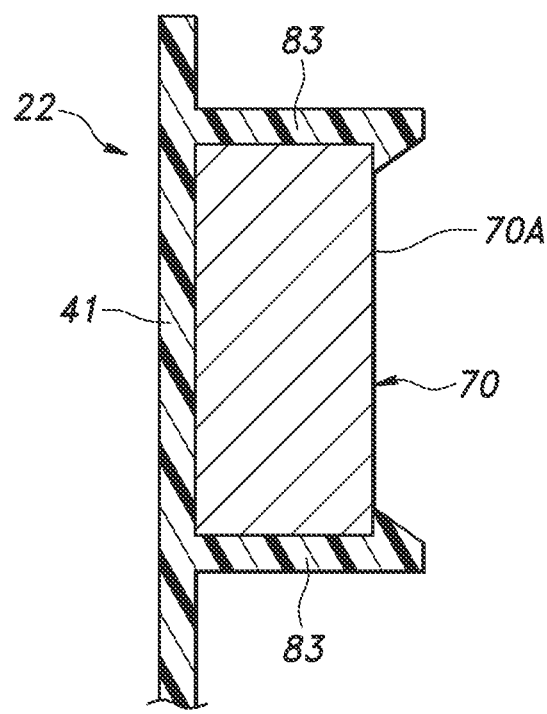
FIG. 11 is yet another example of a mounting structure for mounting a radio wave transmitting/receiving device to a base plate according to the second embodiment of the present invention.

In another example, one of the radio wave transmitting/receiving device 70 and the pressure receiving member 22 is provided with an engagement claw that engages the other of the radio wave transmitting/receiving device 70 and the pressure receiving member 22. For example, as shown in FIG. 11, a plurality of engagement claws 83 may be provided on the back surface of the base plate 41 so as to project therefrom. The engagement claws 83 may engage the corners of the casing 70A of the radio wave transmitting/receiving device 70, or other features of the casing 70A such as recesses and holes formed in the casing 70A.

In another example, the radio wave transmitting/receiving device 70 is fastened to the base plate 41 by a fastening member such as a screw or a clip.

Figure 12:
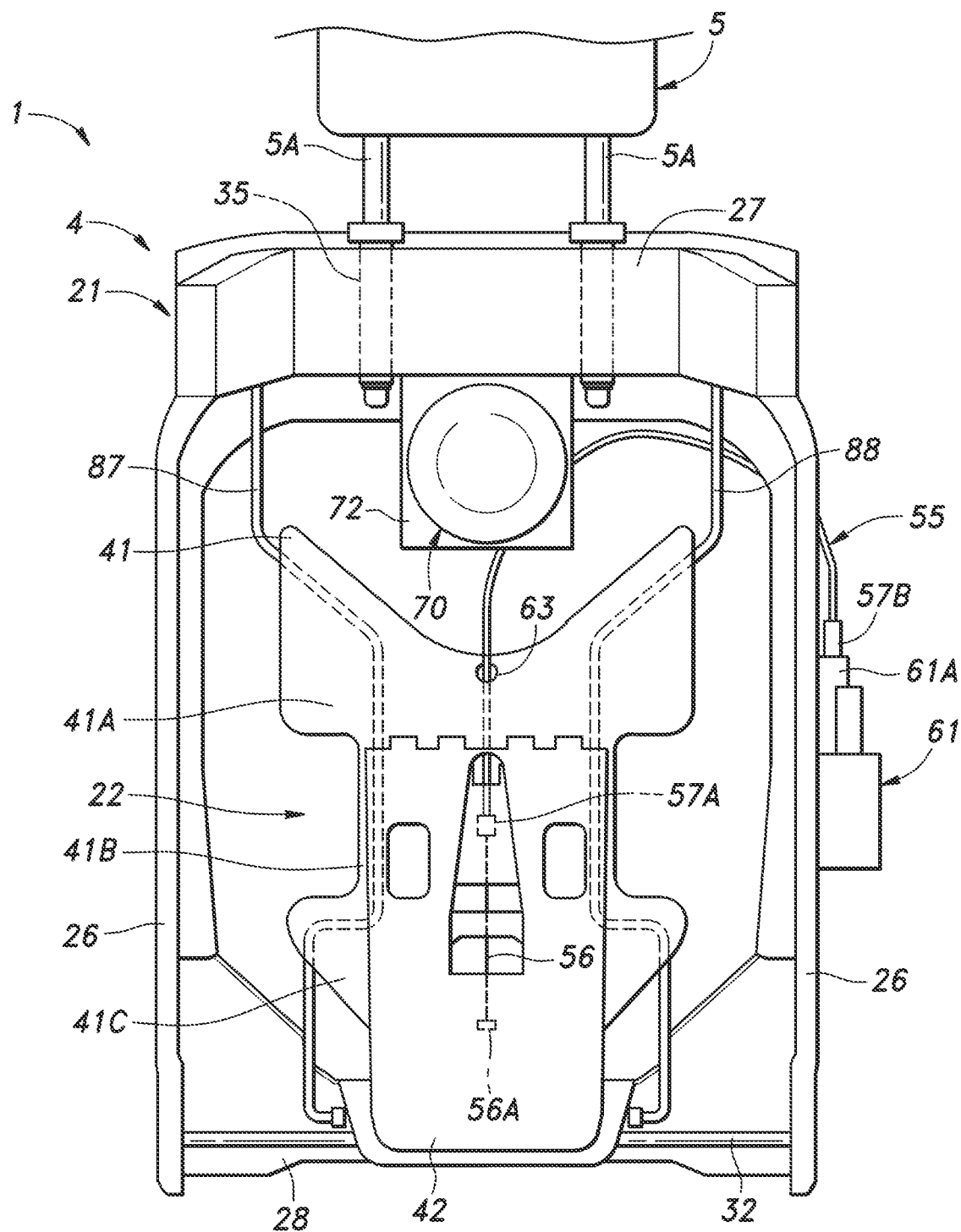
FIG. 12 is a front view of a seatback according to a modified embodiment of the present invention with a pad and a skin member omitted from illustration.

Although the present invention has been described in terms of specific embodiments, the present invention is not limited to such embodiments, and can be modified in various ways. For example, the shape of the seatback frame 21 may be changed depending on the purpose. For example, as shown in FIG. 12, the upper frame portion 27 may be formed of a sheet metal member instead of a pipe member. In this example, the upper frame portion 27 is formed by a channel member that opens toward the rear. The vertical width of the upper frame portion 27 is substantially equal to the vertical length of the support members 35. The support members 35 are passed vertically through the upper frame portion 27. In this example, the cross member 33 is omitted by increasing the vertical width of the upper frame portion 27.

The bracket 72 depends downward from the lower surface of the upper frame portion 27. The lower end of the bracket 72 is a free end. The radio wave transmitting/receiving device 70 is positioned on the front surface of the bracket 72 so as to irradiate radio wave toward the front.

Figure 13:
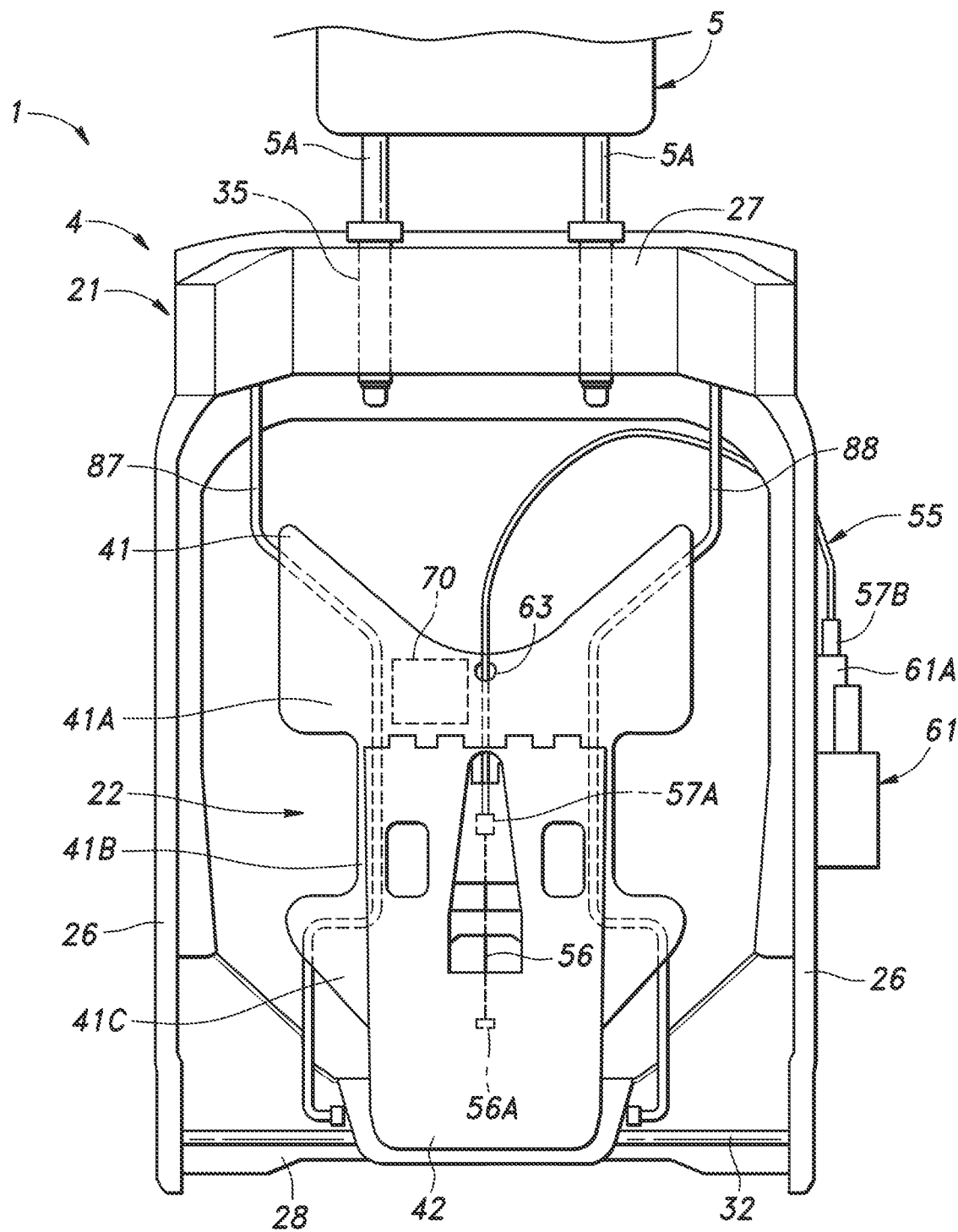
FIG. 13 is a front view of a seatback according to another modified embodiment of the present invention with a pad and a skin member omitted from illustration.

As shown in FIGS. 12 and 13, the pressure receiving member 22 may have any shape, and the elastic member for supporting the pressure receiving member 22 may be connected to any part of the seatback frame 21. As shown in FIG. 12, the base plate 41 has an upper portion 41A, an intermediate portion 41B, and a lower portion 41C from the upper side down. The lateral width of the upper portion 41A is larger than the lateral width of the lower portion 41C, and the lateral width of the lower portion 41C is larger than the lateral width of the intermediate portion 41B. Thus, the width of the base plate 41 changes in the vertical direction. The left and right ends of the upper portion 41A project upward relative to the central part of the upper portion 41A. The central part of the lower portion 41C projects downward relative to the left and right ends of the lower portion 41C.

In FIG. 12, a left and a right elastic member 87, 88 are each connected to the upper frame portion 27 at the upper end thereof and to the lower frame portion 28 at the lower end thereof so as to jointly support the pressure receiving member 22. The elastic members 87 and 88 extend along the back surface of the base plate 41, and are engaged by the hook portions 46 provided on the back surface of the base plate 41.

As shown in FIG. 13, the radio wave transmitting/receiving device 70 may be provided on the base plate 41 at a vertical position corresponding to the largest lateral width of the base plate 41, or provided on the back surface of the upper portion 41A of the base plate 41. As a result, the radio wave transmitting/receiving device 70 can be positioned on the pressure receiving member 22 in a stable manner.

Figure 14:
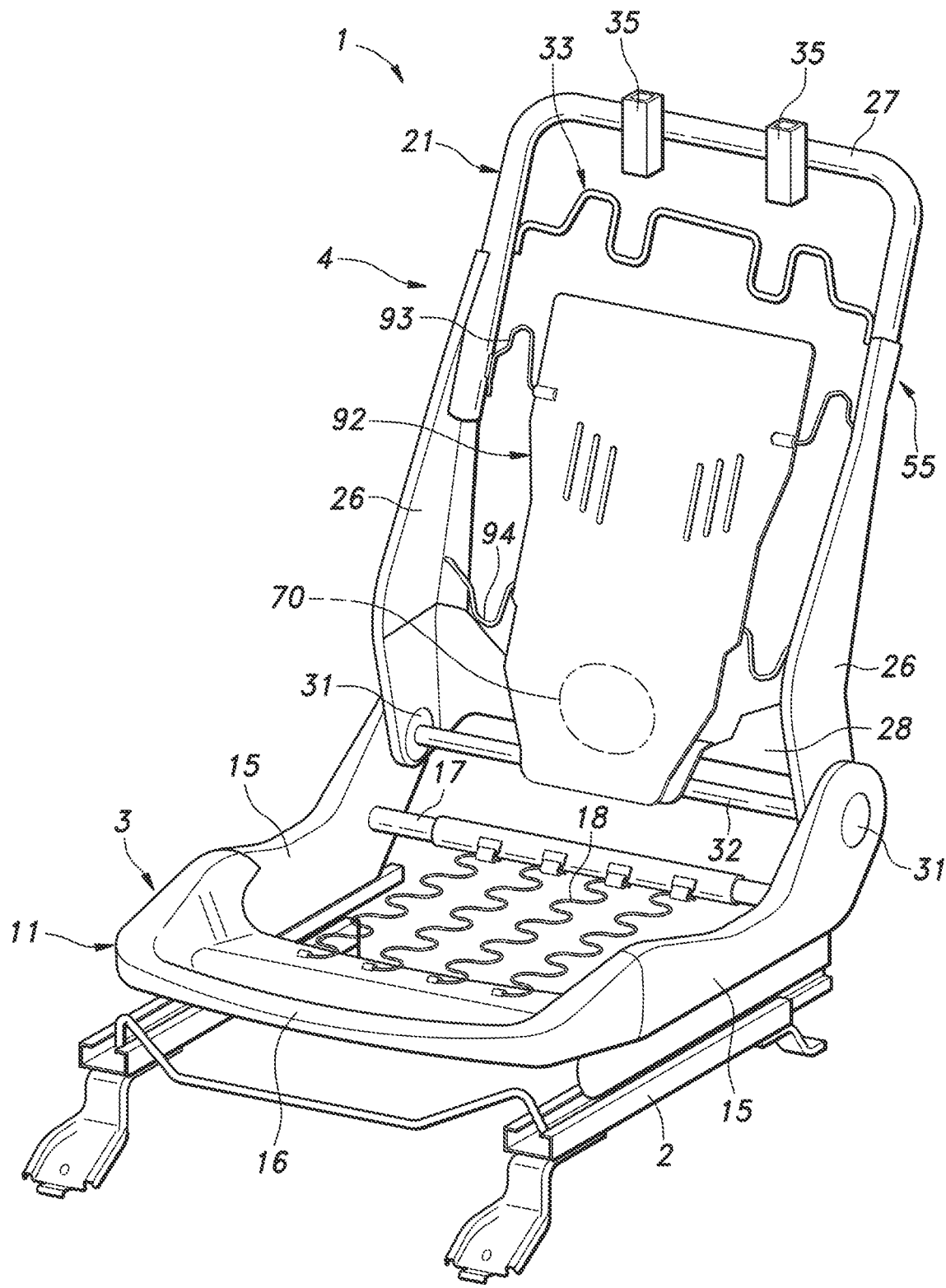
FIG. 14 is a perspective view showing a frame of a seat according to a modified embodiment of the present invention.
Figure 15:
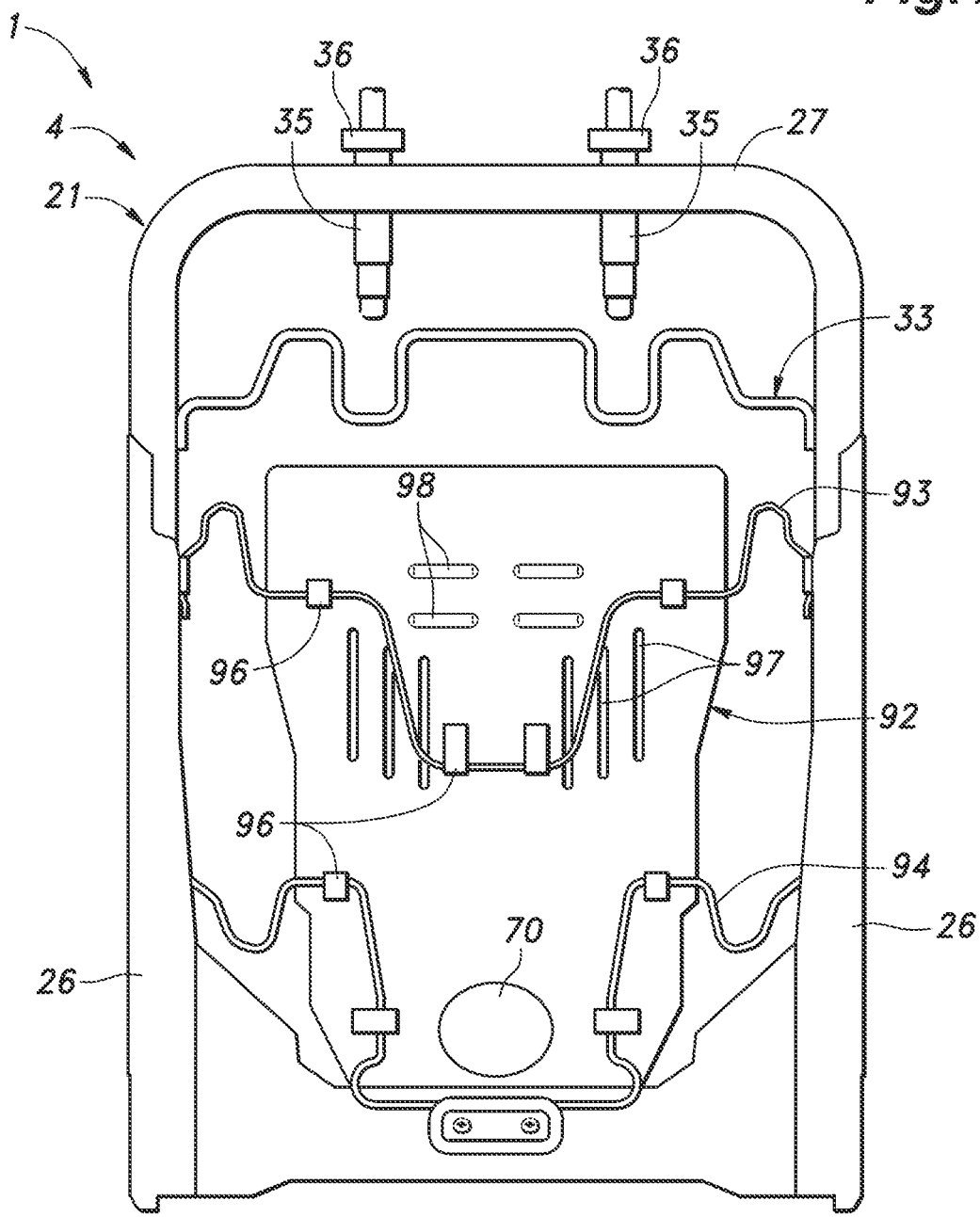
FIG. 15 is a front view of a seatback of the modified embodiment with a pad and a skin member omitted from illustration.

As shown in FIGS. 14 and 15, the pressure receiving member 92 may be formed from a single plate member. The pressure receiving member 92 is supported by the seatback frame 21 via elastic members 93 and 94. The pressure receiving member 92 is flexible and is preferably formed of a resin material. The pressure receiving member 92 is formed of a material having a property to transmit radio wave such as millimeter wave and microwave. The pressure receiving member 92 may be formed of, for example, polycarbonate, syndiotactic polystyrene, polypropylene, acrylonitrile-butadiene-styrene (ABS) resin, or the like.

The elastic members 93 and 94 are preferably made of metal wires having elasticity such as wirework springs. The elastic members 43 and 44 extend laterally and are connected to the left and right side frame portions 15 at the left and right ends thereof, respectively. A plurality of hook portions 96 for engaging the elastic members 93 and 94 are formed on the back surface of the pressure receiving member 92. Preferably, a plurality of openings 97 are formed at appropriate positions of the pressure receiving member 92 for the purpose of increasing flexibility. Further, it is preferable that a plurality of reinforcing ribs 98 are formed at appropriate positions of the pressure receiving member 92 for the purpose of locally increasing the rigidity.

A lower part of the back surface of the pressure receiving member 92 supports a radio wave transmitting/receiving device 70. The radio wave transmitting/receiving device 70 is supported by the pressure receiving member 92 so that the radio wave transmitting and receiving direction is directed forward. The radio wave transmitting/receiving device 70 irradiates the radio wave forward through the pressure receiving member 92, and the radio wave transmitting/receiving device 70 receives the radio wave reflected by the surface of the back of the seated person, and traveling from the front to the rear through the pressure receiving member 92. The radio wave transmitting/receiving device 70 may be supported by the pressure receiving member 92 by using a pocket 81 and an engagement claw 83 similar to those of the second embodiment.

LIST OF REFERENCE NUMERALS

| | |
|---|---|
| 1: seat | 3: seat cushion |
| 4: seatback | 5: headrest |
| 5A: pillar | 21: seatback frame |
| 22: pressure receiving member | 23: pad |
| 24: skin member | 26: side frame portion |
| 27: upper frame portion | 28: lower frame portion |
| 33: cross member | 35: support member |
| 41: base plate | 41A: upper part |
| 41B: intermediate part | 41C: lower part |
| 42: movable plate | 43: first elastic member |
| 44: second elastic member | 47: opening |
| 48: reinforcing rib | 51: locking hole |
| 52: engagement claw | 55: control cable |
| 61A: casing | 70: radio transmitting/receiving device |
| 70A: casing | 72: bracket |
| 72A: main body | 72B: connecting piece |
| 72C: edge wall | 75: recess |
| 81: pocket | 82: fastening member |
| 83: engagement claw | |

The invention claimed is:

1. A vehicle seat including a seat cushion and a seatback connected to a rear part of the seat cushion, wherein the seatback comprises:
   a seatback frame including a left and a right side frame portion extending vertically, and an upper frame portion extending laterally between upper ends of the side frame portions,
   a pressure receiving member consisting of a plate member configured to support a back of a seated person and provided with a radio wave transmissive property, and supported by the seatback frame via an elastic member, and
   a radio wave transmitting/receiving device supported on a back surface of the pressure receiving member to irradiate radio wave to a seated person and receive radio wave reflected by the seated person,
   wherein the radio wave transmitting/receiving device is received in a pocket provided on a back surface of the pressure receiving member.

2. The vehicle seat according to claim 1, wherein one end of a control cable for deforming the pressure receiving member is connected to the pressure receiving member, and the radio wave transmitting/receiving device is positioned so as not to overlap with the control cable in front view.

3. The vehicle seat according to claim 1, wherein the elastic member comprises a metal wire, and the radio wave transmitting/receiving device is positioned so as not to overlap with the elastic member in front view.

4. The vehicle seat according to claim 1, wherein the pressure receiving member is provided with a plurality of reinforcing ribs, and the radio wave transmitting/receiving device is positioned so as not to overlap with the reinforcing ribs in front view.

5. The vehicle seat according to claim 1, wherein the pressure receiving member is provided with a plurality of openings, and the radio wave transmitting/receiving device is positioned so as not to overlap with the openings in front view.

6. The vehicle seat according to claim 1, wherein the radio wave transmitting/receiving device is positioned on the pressure receiving member so as to be laterally offset from a center of the seatback in front view.

7. A vehicle seat including a seat cushion and a seatback connected to a rear part of the seat cushion, wherein the seatback comprises:
- a seatback frame including a left and a right side frame portion extending vertically, and an upper frame portion extending laterally between upper ends of the side frame portions,
- a pressure receiving member consisting of a plate member configured to support a back of a seated person and provided with a radio wave transmissive property, and supported by the seatback frame via an elastic member, and
- a radio wave transmitting/receiving device supported on a back surface of the pressure receiving member to irradiate radio wave to a seated person and receive radio wave reflected by the seated person, wherein one of the radio wave transmitting/receiving device and the pressure receiving member is provided with an engagement claw for engaging another of the radio wave transmitting/receiving device and the pressure receiving member.

8. The vehicle seat according to claim 1, wherein the pressure receiving member has a lateral width which changes along a vertical direction, and the radio wave transmitting/receiving device is provided at a vertical position having a largest lateral width in the pressure receiving member.

9. The vehicle seat according to claim 1, wherein the upper frame portion is provided with a left and a right support member for supporting a left and a right pillar of a headrest, respectively, and the radio wave transmitting/receiving device is positioned laterally between the right and left support members in front view.

* * * * *